US012758436B2

(12) United States Patent
Sakoda

(10) Patent No.: US 12,758,436 B2
(45) Date of Patent: Oct. 13, 2026

(54) ABSORBENT ARTICLE

(71) Applicant: SUMITOMO SEIKA CHEMICALS CO., LTD., Kako-gun (JP)

(72) Inventor: Miki Sakoda, Himeji (JP)

(73) Assignee: Sumitomo Seika Chemicals Co., Ltd., Hyogo (JP)

( * ) Notice: Subject to any disclaimer, the term of this patent is extended or adjusted under 35 U.S.C. 154(b) by 290 days.

(21) Appl. No.: 18/565,470

(22) PCT Filed: May 30, 2022

(86) PCT No.: PCT/JP2022/021926
§ 371 (c)(1),
(2) Date: Nov. 29, 2023

(87) PCT Pub. No.: WO2022/255301
PCT Pub. Date: Dec. 8, 2022

(65) Prior Publication Data

US 2024/0261159 A1 Aug. 8, 2024

(30) Foreign Application Priority Data

May 31, 2021 (JP) ................................ 2021-091474

(51) Int. Cl.
*A61F 13/531* (2006.01)
*A61F 13/15* (2006.01)
*A61F 13/53* (2006.01)

(52) U.S. Cl.
CPC .. *A61F 13/531* (2013.01); *A61F 2013/15406* (2013.01); *A61F 2013/15471* (2013.01);
(Continued)

(58) Field of Classification Search
CPC .................... A61F 12/531; A61F 12/53; A61F 2013/15406; A61F 2013/15471;
(Continued)

(56) References Cited

U.S. PATENT DOCUMENTS 5,180,798 A 1/1993 Nakamura et al.
2007/0093766 A1 4/2007 Yoshino et al.
(Continued)

FOREIGN PATENT DOCUMENTS

CN 1805723 A 7/2006
CN 1886109 A 12/2006
(Continued)

OTHER PUBLICATIONS

Extended European Search Report for App. No. 22816048.7, dated Apr. 7, 2025 (in 8 pages).
(Continued)

*Primary Examiner* — Ariana Zimbouski
(74) *Attorney, Agent, or Firm* — Knobbe, Martens, Olson & Bear, LLP

(57) ABSTRACT

Provided is an absorbent article which exhibits a better permeation rate and in which occurrence of leakage is suppressed. An absorbent article comprising: a liquid-permeable front surface sheet; a liquid-impermeable back surface sheet; and an absorbent body disposed between the front and back surface sheets, wherein the absorbent body contains a water-absorbent resin, and the water-absorbent resin has properties (A)-(C). (A) The amount of saline that can be retained is 45-70 g/g. (B) The amount of saline that can be absorbed under a load of 4.14 kPa is at least 13 ml/g. (C) The five-minute value of no-pressure DW is 50-80 ml/g.

7 Claims, 2 Drawing Sheets

(52) U.S. Cl.
CPC ............. *A61F 2013/530839* (2013.01); *A61F 2013/5315* (2013.01)

(58) Field of Classification Search
CPC .. A61F 2013/530839; A61F 2013/5315; A61F 13/53708; A61F 13/53713; A61F 13/53717; A61F 13/537; A61F 13/53; B01J 2220/68; B01J 20/28011; B01J 20/2805; B01J 20/267; A61L 15/60
See application file for complete search history.

(56) References Cited

U.S. PATENT DOCUMENTS

| | | | |
|---|---|---|---|
| 2014/0031507 | A1* | 1/2014 | Fukudome .............. A61L 15/22 526/317.1 |
| 2016/0213525 | A1 | 7/2016 | Suzuki et al. |
| 2017/0312148 | A1 | 11/2017 | Dobrosielska-Oura et al. |
| 2020/0001270 | A1* | 1/2020 | Chiba ..................... C08F 20/06 |
| 2020/0299423 | A1 | 9/2020 | Hama et al. |
| 2022/0015959 | A1 | 1/2022 | Yabuguchi |
| 2022/0072508 | A1 | 3/2022 | Nishida |

FOREIGN PATENT DOCUMENTS

| | | | | |
|---|---|---|---|---|
| EP | 3954728 | A1 * | 2/2022 | ................ C08J 3/12 |
| EP | 4316441 | A1 | 2/2024 | |
| JP | H03-227301 | A | 10/1991 | |
| JP | 2006-346143 | A | 12/2006 | |
| JP | 2010-116548 | A | 5/2010 | |
| JP | 2014-014666 | A | 1/2014 | |
| JP | 2015-047432 | A | 3/2015 | |
| JP | 2018-047190 | A | 3/2018 | |
| WO | WO-2010004894 | A1 * | 1/2010 | ............. B32B 5/022 |
| WO | WO 2020/184388 | A1 | 9/2020 | |
| WO | WO 2020/218158 | A1 | 10/2020 | |

OTHER PUBLICATIONS

International Search Report received in International Application No., PCT/JP2022/021926, mailed on Aug. 16, 2022.

Chinese Office Action for App. No. 202280037964.6 dated Aug. 1, 2026 (in 10 pages).

* cited by examiner

ABSORBENT ARTICLE

TECHNICAL FIELD

The present invention relates to an absorbent article, and more particularly to an absorbent article to be suitably used for sanitary materials such as disposable diapers, sanitary napkins, and incontinence pads.

BACKGROUND ART

In recent years, water-absorbent resins have been widely used in a field of sanitary materials such as disposable diapers, sanitary napkins, and incontinence pads.

As such a water-absorbent resin, a crosslinked product of a polymer of a water-soluble ethylenically unsaturated monomer, more specifically, a crosslinked product of a polymer of a partially neutralized polyacrylic acid is considered to be a preferable water-absorbent resin because it has various advantages, for example, as follows: it has superior water absorption capacity; it can be produced with a constant quality and at a low cost because of the easy industrial availability of acrylic acid, which is its raw material; and it is less prone to suffering from decomposition or degradation (see, for example, Patent Document 1).

An absorbent article such as a disposable diaper, a sanitary napkin, or an incontinence pad is composed of an absorber that absorbs and retains a body fluid such as urine or menstrual blood excreted from the body, the absorber being positioned mainly in a central portion, a liquid-permeable front sheet (top sheet) positioned on the side of the absorbent article that is brought into contact with the body, and a liquid-impermeable rear sheet (back sheet) positioned opposite from the side that is brought into contact with the body. The absorber is usually composed of hydrophilic fibers such as pulp and a water-absorbent resin.

PRIOR ART DOCUMENT

Patent Document

Patent Document 1: Japanese Patent Laid-open Publication No. H3-227301

SUMMARY OF THE INVENTION

Problems to be Solved by the Invention

In such an absorbent article, a high water retention capacity is required for the water-absorbent resin contained in the absorber. By increasing the water retention capacity of the water-absorbent resin, it is possible to improve a phenomenon in which the liquid once absorbed in the absorber reverses (namely, a phenomenon in which the liquid reverses from the absorber; when touching the absorber with a hand, the user feels uncomfortable wetting). However, in a case where the absorbent surface of the absorbent article is inclined at the time of use of the absorbent article, a liquid excreted repeatedly is not absorbed sufficiently in spite of the high water retention capacity of the water-absorbent resin, so that a problem that the liquid leaks out of the absorbent article may occur.

In addition, when a large amount of the water-absorbent resin becomes a soft gel due to absorption of a liquid and a load is applied to the gel, a so-called "gel blocking phenomenon" occurs, so that liquid diffusibility may be significantly reduced, and the permeation rate of the liquid in the absorber may be reduced. The "gel blocking phenomenon" is a phenomenon in which, particularly when an absorber in which a large amount of water-absorbent resin is densely present absorbs a liquid, the water-absorbent resin present near the surface layer absorbs the liquid to form a soft gel near the surface layer, and the gel becomes dense, so that permeation of the liquid into the absorber is inhibited, and the water-absorbent resin inside cannot efficiently absorb the liquid.

As a method for improving the permeation rate of the liquid in such an absorber, it is conceivable to add a means for improving liquid permeability, but even if the permeation rate is improved by the means for improving liquid permeability, the liquid tends to easily leak out of the absorbent article, and it is difficult to improve the absorption characteristics as an absorbent article in a well-balanced manner.

Under such circumstances, a main object of the present invention is to provide an absorbent article being superior in permeation rate and being inhibited from the occurrence of leakage.

Means for Solving the Problem

The present inventors have conducted intensive studies in order to solve the above problems. When, in an absorbent article including a liquid-permeable front sheet, a liquid-impermeable rear sheet, and an absorber disposed between the front sheet and the rear sheet, a water-absorbent resin having a prescribed physiological saline retention capacity, a prescribed physiological saline absorption capacity under a load of 4.14 kPa, and a prescribed value of non-pressurization DW after 5 minutes is used as a water-absorbent resin, an absorbent article being superior in permeation rate and being inhibited from occurrence of leakage can be obtained. The present invention has been accomplished through further intensive studies based on such findings.

In summary, the present invention provides aspects with the following configurations:

Item 1. An absorbent article comprising a liquid-permeable front sheet, a liquid-impermeable rear sheet, and an absorber disposed between the front sheet and the rear sheet, wherein the absorber comprises a water-absorbent resin, and the water-absorbent resin has the following properties (A) to (C).

(A) A physiological saline retention capacity is 45 g/g or more and 70 g/g or less.

(B) A physiological saline absorption capacity under a load of 4.14 kPa is at least 13 ml/g.

(C) A value of non-pressurization DW after 5 minutes is 50 ml/g or more and 80 ml/g or less.

Item 2. The absorbent article according to item 1, including a means for improving liquid permeability provided at at least one site among the front sheet, the absorber, and a portion between the front sheet and the absorber.

Item 3. The absorbent article according to item 2, wherein the means for improving liquid permeability is at least one selected from the group consisting of an embossed structure, a slit structure, and an arrangement of a liquid-acquisition diffusion sheet between the front sheet and the absorber.

Item 4. The absorbent article according to item 2 or 3, wherein the means for improving liquid permeability is a recessed portion, a groove, or a slit structure formed by cutting out, squeezing, or penetrating the absorber in a thickness direction thereof.

Item 5. The absorbent article according to any one of items 2 to 4, wherein the means for improving liquid permeability is an embossed structure provided in the absorber.

Item 6. The absorbent article according to any one of items 2 to 5, wherein the means for improving liquid permeability is an arrangement of a liquid-acquisition diffusion sheet made of a hydrophilic nonwoven fabric having a basis weight of 15 $g/m^2$ or more and 75 $g/m^2$ or less between the front sheet and the absorber.

Item 7. The absorbent article according to any one of items 1 to 6, wherein the absorber further comprises hydrophilic fibers.

Advantages of the Invention

According to the present invention, it is possible to provide an absorbent article being superior in permeation rate and being inhibited from the occurrence of leakage. Furthermore, the present invention can also provide a water-absorbent resin, an absorber prepared using the water-absorbent resin, and an absorbent article.

EMBODIMENTS OF THE INVENTION

In the present description, the term “comprising” includes “consisting essentially of” and “consisting of”. In addition, in the present description, the term “(meth) acryl” means “acryl or methacryl”, the term “(meth)acrylate” means “acrylate or methacrylate”, and the term (poly)” means both cases with and without the prefix “poly”. In addition, in the present description, the term “water-soluble” means that a solubility of 5% by mass or more is exhibited in water at 25° C.

In the present description, two numerical values joined by “to” means a numerical range including the numerical values before and after “to” as a lower limit value and an upper limit value, respectively. When a plurality of lower limit values and a plurality of upper limit values are described separately, an arbitrary lower limit value and an arbitrary upper limit value may be selected and joined by “to”.

The absorbent article of the present invention comprises a liquid-permeable front sheet, a liquid-impermeable rear sheet, and an absorber disposed between the front sheet and the rear sheet. The absorber comprises a water-absorbent resin, and the water-absorbent resin has the following characteristics (A) to (C).

(A) A physiological saline retention capacity is 45 g/g or more and 70 g/g or less.

(B) A physiological saline absorption capacity under a load of 4.14 kPa is at least 13 ml/g.

(C) A value of non-pressurization DW after 5 minutes is 50 ml/g or more and 80 ml/g or less.

Owing to including these configurations, the absorbent article of the present invention is superior in permeation rate and can inhibit the occurrence of leakage. The absorbent article of the present invention will be hereinafter described in detail.

The absorbent article of the present invention includes an absorber. The absorbent article of the present invention includes, in addition to the absorber, a core wrap that retains the shape of the absorbent; a liquid-permeable sheet disposed on the outermost part on a side from which an absorption target liquid is infiltrated; a liquid-impermeable sheet disposed on the outermost part on a side opposite from the side from which the absorption target liquid is infiltrated; and so on. Examples of the absorbent article include diapers (for example, disposable diapers), toilet training pants, incontinence pads, sanitary materials (sanitary napkins, tampons, and the like), sweat pads, pet sheets, portable toilet members, and animal excrement treatment materials. The absorbent article may be disposable. Hereinafter, the absorber and the absorbent article according to the present invention will be described in detail.

Figure 1:
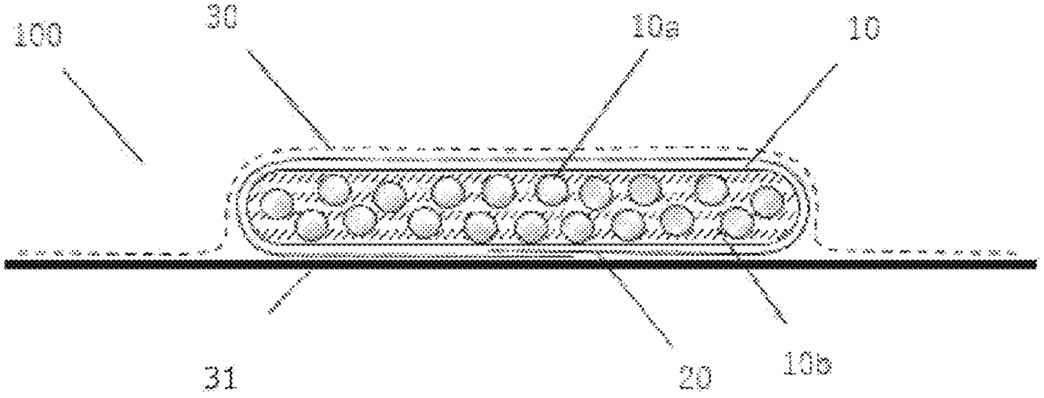
FIG. 1 is one example of a schematic cross-sectional view of an absorbent article.

FIG. 1 is a cross-sectional view illustrating one example of an absorbent article 100. An absorbent article 100 illustrated in FIG. 1 includes an absorber 10, a core wrap 20, a liquid-permeable sheet 30, and a liquid-impermeable sheet 31. In the absorbent article 100, the liquid-impermeable sheet 31, the absorber 10 whose outer periphery is covered with the core wrap 20, and the liquid-permeable sheet 30 are laminated in this order.

The absorber 10 according to the present invention includes a water-absorbent resin 10*a* according to the present embodiment and a fiber layer 10*b* comprising hydrophilic fibers, which is preferably employed. Note that the absorber 10 may or may not contain hydrophilic fibers. The water-absorbent resin 10*a* is, for example, supported and dispersed in the fiber layer 10*b*. Examples of the configuration of the absorber 10 include a sheet-like structure in which a water-absorbent resin is fixed on a nonwoven fabric or between a plurality of nonwoven fabrics, a mixed dispersion obtained by mixing a water-absorbent resin and hydrophilic fibers to attain a uniform composition, a sandwich structure in which a water-absorbent resin is sandwiched between layered hydrophilic fibers, and a structure in which a water-absorbent resin and hydrophilic fibers are wrapped with tissue.

The planar shape of the absorber 10 is appropriately determined according to the intended use or the shape of the absorbent article, and examples thereof include a substantially rectangular shape, an elliptical shape, an hourglass shape, and a battledore shape, and the absorber may have a notch or the like for improving fitting. Furthermore, the internal structure of the absorber 10 is also appropriately determined according to the purpose. For example, the absorber 10 not only may be composed of a single absorber, but also may be composed of a combination of a plurality of absorbers (divided on a flat plane, vertically divided, or the like), or may have, within the absorber, a quantitative distribution gradient of the water-absorbent resin and other components (uniform distribution; quantitative distribution corresponding to a liquid pouring part; or the like).

The water-absorbent resin in the absorber 10 has a basis weight of 50 $g/m^2$ or more and 400 $g/m^2$ or less. From the viewpoint of more suitably exhibiting the effect of the present invention, the basis weight is preferably 100 $g/m^2$ or more, more preferably 120 $g/m^2$ or more, and still more preferably 140 g/m$^2$ or more, and is preferably 300 g/m$^2$ or less, more preferably 250 g/m$^2$ or less, and still more preferably 200 g/m$^2$ or less.

The content of the water-absorbent resin in the absorber is preferably 5 to 100% by mass, more preferably 10 to 95% by mass, still more preferably 20 to 90% by mass, and further preferably 30 to 80% by mass.

The hydrophilic fiber may be at least one selected from the group consisting of finely pulverized wood pulp, cotton, cotton linters, rayon, cellulose acetates, polyamides, polyesters, and polyolefins. More specifically, examples thereof include cellulose fibers obtained from wood such as fluff pulp, mechanical pulp, chemical pulp, and semi-chemical pulp; artificial cellulose fibers such as rayon and acetate, and fibers made of synthetic resin, such as polyamide, polyester, or polyolefin, subjected to hydrophilization treatment. The average fiber length of the hydrophilic fibers is usually 0.1 to 10 mm, or may be 0.5 to 5 mm.

The absorber according to the present invention may further contain additives such as an inorganic powder (for example, amorphous silica), a deodorant, a pigment, a dye, an antibacterial agent, a fragrance, and a pressure-sensitive adhesive. These additives can impart various functions to the absorber. When the water-absorbent resin contains inorganic particles, the absorber may contain an inorganic powder separately from the inorganic particles in the water-absorbent resin. Examples of the inorganic powder include silicon dioxide, zeolite, kaolin, and clay.

The liquid-permeable sheet 30 is disposed on the outermost part on a side from which an absorption target liquid is infiltrated. The liquid-permeable sheet 30 is disposed on the core wrap 20 in contact with the core wrap 20. The absorber 10 is made to retain its shape due to being enclosed in the core wrap 20. In order to enhance the form retention property before and during use of the absorber, an adhesive binder may be blended. The liquid-impermeable sheet 31 is disposed on the outermost part on a side opposite from the liquid-permeable sheet 30 in the absorbent article 100. The liquid-impermeable sheet 31 is disposed below the core wrap 20 in contact with the core wrap 20. The liquid-permeable sheet 30 and the liquid-impermeable sheet 31 each have, for example, a main surface wider than the main surface of the absorber 10, and outer edges of the liquid-permeable sheet 30 and the liquid-impermeable sheet 31 extend around the absorber 10 and the core wrap 20.

The size relationship among the absorber 10, the core wrap 20, the liquid-permeable sheet 30, and the liquid-impermeable sheet 31 is not particularly limited, and is appropriately adjusted according to the use or the like of the absorbent article.

The liquid-permeable sheet 30 may be a sheet formed of a resin or fiber commonly used in the art. From the viewpoint of liquid permeability, flexibility, and strength when the liquid-permeable sheet 30 is used in an absorbent article, the liquid-permeable sheet 30 may contain, for example, synthetic resins such as polyolefins such as polyethylene (PE) and polypropylene (PP); polyesters such as polyethylene terephthalate (PET), polytrimethylene terephthalate (PTT), and polyethylene naphthalate (PEN); polyamides such as nylon; and rayon, regenerated fibers such as cupra, acetate, or synthetic fibers containing these synthetic resins, or the liquid-permeable sheet 30 may be natural fibers including cotton, silk, hemp, or pulp (cellulose). The liquid-permeable sheet 30 may contain synthetic fibers from the viewpoint of, for example, increasing the strength of the liquid-permeable sheet 30. In particular, the synthetic fibers may be polyolefin fibers, polyester fibers, or a combination thereof. These materials may be used alone or in combination of two or more.

The liquid-permeable sheet 30 may be a nonwoven fabric, a porous sheet, or a combination thereof. Nonwoven fabric is a sheet in which fibers are entwined instead of being woven. The nonwoven fabric may be a nonwoven fabric (short-fiber nonwoven fabric) composed of short fibers (that is, staples), or may be a nonwoven fabric (long-fiber nonwoven fabric) composed of long fibers (that is, filaments). In general, staples may have a fiber length of several hundred millimeters or shorter, but its length is not limited thereto.

The liquid-permeable sheet 30 may be a thermally bonded nonwoven fabric, an air-through nonwoven fabric, a resin bonded nonwoven fabric, a spunbond nonwoven fabric, a melt-blown nonwoven fabric, an air-laid nonwoven fabric, a spunlace nonwoven fabric, a point-bonded nonwoven fabric, or a laminate of two or more of nonwoven fabrics selected from these nonwoven fabrics. These nonwoven fabrics can be, for example, nonwoven fabrics formed of the above-described synthetic fibers or natural fibers. The laminate of two or more nonwoven fabrics may be, for example, a spunbond/melt-blown/spunbond nonwoven fabric that is a composite nonwoven fabric including a spunbond nonwoven fabric, a melt-blown nonwoven fabric, and a spunbond nonwoven fabric, which are laminated in this order. From the viewpoint of inhibiting liquid leakage, the liquid-permeable sheet 30 may be a thermally bonded nonwoven fabric, an air-through nonwoven fabric, a spunbond nonwoven fabric, or a spunbond/melt-blown/spunbond nonwoven fabric.

The nonwoven fabric to be used as the liquid-permeable sheet 30 desirably has appropriate hydrophilicity from the viewpoint of liquid absorption performances of the absorbent article. From this viewpoint, the liquid-permeable sheet 30 may be a nonwoven fabric having a hydrophilicity of 5 to 200 as measured in accordance with the measurement method of Pulp and Paper Test Method No. 68 (2000) prescribed by Japan Technical Association of the Pulp and Paper Industry. The hydrophilicity of the nonwoven fabric may be 10 to 150. For details of the Pulp and Paper Test Method No. 68, for example, WO2011/086843 can be referred to.

The hydrophilic nonwoven fabric as described above may be one formed of fibers, such as rayon fibers, showing appropriate hydrophilicity, or may be one formed of fibers obtained by hydrophilizing hydrophobic chemical fibers such as polyolefin fibers and polyester fibers. Examples of the method for obtaining a nonwoven fabric containing a hydrophilized hydrophobic chemical fiber include a method for obtaining a nonwoven fabric by a spunbond method using a mixture of a hydrophobic chemical fiber with a hydrophilizing agent, a method for entraining a hydrophilizing agent when a spunbond nonwoven fabric is produced with a hydrophobic chemical fiber, and a method for impregnating a spunbond nonwoven fabric obtained using a hydrophobic chemical fiber with a hydrophilizing agent. As the hydrophilizing agent, an anionic surfactant such as an aliphatic sulfonic acid salt or a higher alcohol sulfuric acid ester salt, a cationic surfactant such as a quaternary ammonium salt, a nonionic surfactant such as a polyethylene glycol fatty acid ester, a polyglycerin fatty acid ester, or a sorbitan fatty acid ester, a silicone-based surfactant such as a polyoxyalkylene-modified silicone, and a stain release agent composed of a polyester-based resin, a polyamide-based resin, an acryl-based resin, or a urethane-based resin are used.

The liquid-permeable sheet 30 may be a nonwoven fabric that is moderately bulky and has a large basis weight from the viewpoint of being able to impart favorable liquid permeability, flexibility, strength, and cushioning property to the absorbent article and from the viewpoint of increasing the liquid permeation rate of the absorbent article. The basis weight of the nonwoven fabric to be used for the liquid-permeable sheet 30 may be 5 to 200 g/m$^2$, 8 to 150 g/m$^2$, or 10 to 100 g/m$^2$. The thickness of the nonwoven fabric to be used for the liquid-permeable sheet 30 may be 20 to 1400 μm, 50 to 1200 μm, or 80 to 1000 μm.

In addition, the liquid-permeable sheet 30 may be formed of two or more sheets in order to improve liquid diffusibility, and the surface thereof may be embossed or perforated. The embossing and the perforating can be performed by known methods. In addition, the liquid-permeable sheet 30 may contain a skin lotion, a moisturizing agent, an antioxidant, an anti-inflammatory agent, a pH adjusting agent, and the like in order to reduce the irritation to the skin. The shape of the liquid-permeable sheet 30 depends on the shapes of the absorber and the absorbent article, but may be a shape in which the absorber 10 is covered such that liquid leakage does not occur.

The core wrap 20 is disposed, for example, to cover the outer periphery of the absorber 10. The absorber 10 is disposed inside the core wrap 20. Examples of the core wrap 20 include tissue and nonwoven fabric. The core wrap 20 has, for example, a main surface having the same size as that of the absorber 10. The absorber 10 illustrated in FIG. 1 is made to retain its shape due to being enclosed in the core wrap 20. The method of making the absorber retain its shape by the core wrap is not limited thereto, and for example, the absorber may be sandwiched between two upper and lower separate sheets of core wrap, or the core wrap may form a bag and the absorber may be disposed inside the bag.

In order to enhance the form retention property before and during use of the absorber, an adhesive binder may be blended. Examples of the adhesive binder include thermally fusible synthetic fibers, hot-melt adhesives, and adhesive emulsions.

Examples of the thermally fusible synthetic fiber include full-melt binders such as polyethylene, polypropylene, and an ethylene-propylene copolymer; and partial-melt binders formed of polypropylene and polyethylene in a side-by-side or core-and-sheath structure. In the aforementioned partial-melt binder, only a polyethylene portion is thermally fused. Examples of the hot-melt adhesive include a blend of a base polymer such as an ethylene-vinyl acetate copolymer, a styrene-isoprene-styrene block copolymer, a styrene-butadiene-styrene block copolymer, a styrene-ethylene-butylene-styrene block copolymer, a styrene-ethylene-propylene-styrene block copolymer, or an amorphous polypropylene with a tackifier, a plasticizer, an antioxidant, or the like.

Examples of the adhesive emulsion include a polymer of at least one or more monomers selected from the group consisting of methyl methacrylate, styrene, acrylonitrile, 2-ethylhexyl acrylate, butyl acrylate, butadiene, ethylene, and vinyl acetate. These adhesive binders may be used singly, or two or more of them may be used in combination.

The liquid-impermeable sheet 31 is disposed on the outermost part on a side opposite from the liquid-permeable sheet 30 in the absorbent article 100. The liquid-impermeable sheet 31 is disposed below the core wrap 20 in contact with the core wrap 20. The liquid-impermeable sheet 31 has, for example, a main surface wider than the main surface of the absorber 10, and an outer edge of the liquid-impermeable sheet 31 extends around the absorber 10 and the core wrap 20. The liquid-impermeable sheet 31 prevents the liquid absorbed by the absorber 10 from leaking from the liquid-impermeable sheet 31 side to the outside.

Examples of the liquid-impermeable sheet 31 include a sheet made of a synthetic resin such as polyethylene, polypropylene, or polyvinyl chloride, a sheet made of a nonwoven fabric such as spunbond/melt-blown/spunbond (SMS) nonwoven fabric in which a water-resistant melt-blown nonwoven fabric is sandwiched between high-strength spunbond nonwoven fabrics, and a sheet made of a composite material of these synthetic resins and a nonwoven fabric (for example, a spunbond nonwoven fabric or a spunlace nonwoven fabric). The liquid-impermeable sheet 31 may have air permeability from the viewpoint of reducing stuffiness at the time of wearing to reduce discomfort given to the wearer. As the liquid-impermeable sheet 31, a sheet made of a synthetic resin mainly composed of a low density polyethylene (LDPE) resin may be used. From the viewpoint of securing flexibility so as not to impair the comfortability in wearing the absorbent article, the liquid-impermeable sheet 31 may be, for example, a sheet made of a synthetic resin and having a basis weight of 10 to 50 g/m$^2$. In addition, in order to impart air permeability to the liquid-impermeable sheet 31, for example, a filler may be blended in the resin sheet, or the liquid-impermeable sheet 31 may be embossed. As the filler, calcium carbonate or the like is used.

In addition to the liquid-permeable sheet, the absorber, the liquid-impermeable sheet, and the core wrap described above, other members may be appropriately present in the absorbent article 100 according to the application or function. Examples thereof include an outer cover nonwoven fabric and a leg gather.

(Outer Cover Nonwoven Fabric)

An outer cover nonwoven fabric may be disposed on a side opposite to the absorber-facing side of the liquid-impermeable sheet 31. The outer cover nonwoven fabric may be bonded to the liquid-impermeable sheet 31 using, for example, an adhesive. The outer cover nonwoven fabric may be formed of one or more layers, or may be a soft material. The outer cover nonwoven fabric may be imparted with a soft touch, may have a pattern printed thereon, may have a plurality of connected portions, may be embossed, or may have a three-dimensional form in order to appeal to consumers' desire to purchase, or according to other reasons.

(Leg Gather)

The absorbent article 100 of the present invention may include a leg gather which is provided with an elastic member having stretchability, disposed outside both end portions in the width direction of the absorber 10, and disposed substantially in parallel with the longitudinal direction of the absorber 10. The length of the leg gather is set to be equal to or slightly longer than the length around the wearer's leg. The stretch rate of the leg gather is appropriately set from the viewpoint of preventing leakage of an excreted liquid and also reducing tightness at the time of wearing for a long time.

(Front/Back Gather)

The absorbent article 100 of the present invention may include a front/back gather which is provided with an elastic member that expands and contracts in the width direction, and is disposed in the vicinity of both end portions in the longitudinal direction of the absorbent article.

The absorbent article 100 includes a front/back gather that can rise up above the side edges in the width direction of the absorber 10. That is, on each of both sides in the longitudinal direction of the absorbent article, a sheet member of a front/back gather having a gather elastic member is disposed to form a front/back gather.

The member for the front/back gather is usually made of a liquid-impermeable or water repellent material, preferably a moisture-permeable material. Examples thereof include a liquid-impermeable or water repellent porous sheet, a liquid-impermeable or water repellent nonwoven fabric, and a laminate of the porous sheet and the nonwoven fabric. Examples of the nonwoven fabric include a thermally bonded nonwoven fabric, a spunbond nonwoven fabric, a melt-blown nonwoven fabric, a spunlace nonwoven fabric, and a spunbond/melt-blown/spunbond nonwoven fabric. The basis weight of the member may be 5 to 100 g/m$^2$, 8 to 70 g/m$^2$, or 10 to 40 g/m$^2$.

The absorbent article 100 can be manufactured by, for example, a method including disposing the absorber 10 in the core wrap 20, and disposing them between the liquid-permeable sheet 30 and the liquid-impermeable sheet 31. A laminate, in which the liquid-impermeable sheet 31, the core wrap 20, the absorber 10, the core wrap 20, and the liquid-permeable sheet 30 are laminated in this order, is pressurized, as necessary.

The respective members constituting the absorbent article 100 may be adhered. For example, when the absorber 10 and the liquid-permeable sheet 30 are adhered to each other, a liquid is more smoothly guided to the absorber, and therefore an absorbent article superior in preventing liquid leakage is likely to be afforded. In a case where the absorber 10 is covered or sandwiched by the core wrap 20, it is preferable that at least the core wrap 20 and the liquid-permeable sheet 30 be adhered to each other, and it is more preferable that the core wrap 20 and the absorber 10 be adhered to each other as well. Examples of the adhering method include publicly known methods such as an adhesive, heat sealing, and ultrasonic sealing. Examples of the method of adhesion include a method involving applying a hot-melt adhesive to the liquid-permeable sheet 30 in a shape such as a vertical stripe shape or a spiral shape at prescribed intervals in the width direction of the liquid-permeable sheet; and a method involving using a water-soluble adhesive selected from among starch, carboxymethyl cellulose, polyvinyl alcohol, polyvinylpyrrolidone, and other water-soluble polymers. Furthermore, when the absorber 10 contains thermally fusible synthetic fibers, a method involving thermal fusion thereof may be employed.

The shape of the absorbent article 100 is appropriately determined according to the intended use, and for example when the absorbent article is a urine pad or a sanitary napkin, examples of the shape include a substantially rectangular shape, an elliptical shape, an hourglass shape, and a battledore shape.

In the absorbent article of the present invention, it is preferable that a means for improving liquid permeability is provided at at least one site among the front sheet, the absorber, and a portion between the front sheet and the absorber. The means for improving liquid permeability is a means for improving the liquid permeability between the front sheet and the absorber due to including the means, and examples thereof include means such as an embossed structure, a slit structure, and an arrangement of a liquid-acquisition diffusion sheet. The means for improving liquid permeability is preferably an embossed structure and/or an arrangement of a liquid-acquisition diffusion sheet. Including the means for improving liquid permeability makes it possible to further improve the absorption characteristics (permeation rate, leakage performance, etc.) of the absorbent article.

The embossed structure is specifically an uneven shape formed by embossing the surface of the front sheet or the absorber, and the formation of the uneven shape facilitates permeation of a liquid. The pattern in a plan view of the embossed structure is not particularly limited, and may be, for example, a lattice pattern.

The slit structure is a structure in which a slit-shaped hole is provided in at least a part of the absorber. The means for improving liquid permeability may be a recessed portion, a groove, or a slit structure formed by cutting out, squeezing, or penetrating the absorber in a thickness direction thereof. By arranging the slit such that it serves as a liquid flow path, liquid diffusion along the flow path can be promoted, so that the liquid easily permeates. The slit structure may be provided, for example, in the central part of the absorber in a linear shape from the intermediate point to both ends in the longitudinal direction. When the absorber is viewed in a plan view, the ratio of the slit structure to the area (100%) of the absorber is preferably about 2 to 30%.

The liquid-acquisition diffusion sheet is disposed between the front sheet and the absorber. The liquid that has permeated through the liquid-permeable sheet 30 can be quickly moved toward the absorber 10. For adhesion between the liquid-acquisition diffusion sheet and the liquid-permeable sheet 30, a hot-melt adhesive may be used, or heat embossing or ultrasonic welding may be used. As the liquid-acquisition diffusion sheet, a resin film having a large number of permeation holes may be used in addition to or instead of the use of a nonwoven fabric. As the nonwoven fabric, materials the same as those described in the section of the liquid-permeable sheet 30 can be used, but a material higher in hydrophilicity or higher in fiber density than the liquid-permeable sheet 30 is preferable because it is superior in liquid transfer characteristics toward the absorber.

The liquid-acquisition diffusion sheet is usually disposed in a center portion over a shorter width than the absorber 10, but may be disposed over the entire width. The length of the liquid-acquisition diffusion sheet in the front-back direction may be substantially equal to the entire length of the absorbent article, may be substantially equal to the entire length of the absorber 10, or may be a length in a range assuming a portion to which the liquid is to be charged. The liquid-acquisition diffusion sheet preferably has a basis weight within a range of 15 to 75 g/m$^2$.

The water-absorbent resin to be used in the absorbent article of the present invention is characterized by having the following properties (A) to (C). The absorbent article of the present invention using a water-absorbent resin having such characteristics is superior in permeation rate and can inhibit the occurrence of leakage. The water-absorbent resin will hereinafter be described in detail.

(A) A physiological saline retention capacity is 45 g/g or more and 70 g/g or less.

(B) A physiological saline absorption capacity under a load of 4.14 kPa is at least 13 ml/g.

(C) A value of non-pressurization DW after 5 minutes is 50 ml/g or more and 80 ml/g or less.

From the viewpoint of more suitably exhibiting the effect of the present invention, the physiological saline retention capacity of the water-absorbent resin is preferably 46 g/g or more, more preferably 47 g/g or more, and still more preferably 48 g/g or more, and is preferably 70 g/g or less, more preferably 68 g/g or less, and still more preferably 65 g/g or less.

From the viewpoint of more suitably exhibiting the effect of the present invention, the physiological saline absorption capacity under a load of 4.14 kPa of the water-absorbent resin is preferably 13 ml/g or more, more preferably 15 ml/g or more, and still more preferably 17 ml/g or more, and is preferably 33 ml/g or less, more preferably 27 ml/g or less, and still more preferably 23 ml/g or less.

From the viewpoint of more suitably exhibiting the effect of the present invention, the value of non-pressurization DW after 5 minutes of the water-absorbent resin is preferably 53 ml/g or more, more preferably 55 ml/g or more, and still more preferably 60 ml/g or more, and is preferably 78 ml/g or less, more preferably 76 ml/g or less, and still more preferably 74 ml/g or less.

With the water-absorbent resin, the number of the addition of a liquid until the occurrence of leakage measured by a slope absorption test is preferably 4 or more. The number of addition is, for example, 7 times or less. The amount of the liquid absorbed until the occurrence of leakage is preferably 260 g or more, and more preferably 290 g or more. The amount of the liquid absorbed before the occurrence of leakage is, for example, 550 g or less, 520 g or less, or 490 g or less.

The methods for measuring the physiological saline retention capacity, the physiological saline absorption capacity under a load of 4.14 kPa, and the value of non-pressurization DW after 5 minutes of the water-absorbent resin, and the method of the slope absorption test are as described in EXAMPLE, respectively.

The water-absorbent resin is constituted of a product obtained by crosslinking a polymer of a water-soluble ethylenically unsaturated monomer, namely, a crosslinked polymer having a structural unit derived from a water-soluble ethylenically unsaturated monomer.

The water-absorbent resin to be used in the present invention may have various shapes. Examples of the shape of the water-absorbent resin include a granular shape, a substantially spherical shape, an indefinitely crushed shape, a plate shape, a fibrous shape, a flake shape, and a shape in which these resins are aggregated. The water-absorbent resin preferably has a granular shape, a substantially spherical shape, an indefinitely crushed shape, a fibrous shape, a shape in which these resins are aggregated, or the like.

The water-absorbent resin not only may be in a form in which each particle is composed of a single particle, but also may be in a form (secondary particle) in which fine particles (primary particles) are aggregated. Examples of the shape of the primary particles include a substantially spherical shape, an indefinitely crushed shape, and a plate shape. Examples of the primary particles produced by reversed phase suspension polymerization include substantially spherical single particles having a smooth surface shape such as a perfect spherical shape and an ellipsoidal shape. The primary particles having such a shape and having a smooth surface shape thus have high flowability as a powder, and aggregated particles are easily densely packed and thus are less prone to be broken even when subjected to impact, so that a water-absorbent resin having high particle strength is provided.

The median particle diameter of the water-absorbent resin is preferably 200 μm or more, 250 μm or more, 280 μm or more, 300 μm or more, or 320 μm or more from the viewpoint of more suitably exhibiting the effect of the present invention. From the same point of view, the median particle diameter is preferably 700 μm or less, 600 μm or less, 550 μm or less, 500 μm or less, 450 μm or less, or 400 μm or less. That is, the median particle diameter is preferably 200 to 700 μm, preferably 200 to 600 μm, more preferably 250 to 500 μm, still more preferably 300 to 450 μm, and further preferably 320 to 400 μm.

The median particle diameter of the particulate water-absorbent resin can be measured using JIS standard sieves, and specifically, is a value measured by the method described in EXAMPLES.

As the method of polymerizing the water-soluble ethylenically unsaturated monomer, for example, an aqueous solution polymerization method, an emulsion polymerization method, and a reversed phase suspension polymerization method, which are typical polymerization methods, may be used. In the aqueous solution polymerization method, polymerization is carried out by heating an aqueous solution of a water-soluble ethylenically unsaturated monomer with stirring, as necessary. In the reversed phase suspension polymerization method, polymerization is carried out by heating a water-soluble ethylenically unsaturated monomer with stirring in a hydrocarbon dispersion medium. The reversed phase suspension polymerization method is preferably used from the viewpoint of enabling precise polymerization reaction control and control of wide-ranging particle diameter.

A specific embodiment of a method for producing a water-absorbent resin will be described below taking the reversed phase suspension polymerization method as an example.

Specific examples of the method for producing a water-absorbent resin include a method for producing a water-absorbent resin by performing reversed phase suspension polymerization of a water-soluble ethylenically unsaturated monomer in a hydrocarbon dispersion medium, the method including a step of performing polymerization in the presence of a radical polymerization initiator and a step of post-crosslinking a hydrous gel obtained by the polymerization in the presence of a post-crosslinking agent. In the method for producing a water-absorbent resin, an internal crosslinking agent may be added to the water-soluble ethylenically unsaturated monomer as necessary to form a hydrous gel having an internally crosslinked structure.

<Polymerization Step>

[Water-Soluble Ethylenically Unsaturated Monomer]

Examples of the water-soluble ethylenically unsaturated monomer include (meth)acrylic acid and salts thereof; 2-(meth)acrylamido-2-methylpropanesulfonic acid and salts thereof; nonionic monomers such as (meth)acrylamide, N,N-dimethyl(meth)acrylamide, 2-hydroxyethyl (meth)acrylate, N-methylol(meth)acrylamide, and polyethylene glycol mono(meth)acrylate; and amino group-containing unsaturated monomers such as N,N-diethylaminoethyl (meth)acrylate, N,N-diethylaminopropyl (meth)acrylate, and diethylaminopropyl (meth)acrylamide, as well as quaternary compounds thereof. Preferred among these water-soluble ethylenically unsaturated monomers are (meth)acrylic acid and salts thereof, (meth)acrylamide, and N,N-dimethyl(meth)acrylamide, and more preferred are (meth)acrylic acid and salts thereof, from the viewpoint of being readily industrially available. These water-soluble ethylenically unsaturated monomers may be used alone or in combination of two or more.

Among these water-soluble ethylenically unsaturated monomers, acrylic acid and salts thereof are widely used as raw materials of water-absorbent resins. Copolymers of acrylic acid and/or salts thereof with other water-soluble ethylenically unsaturated monomers as mentioned above may also be used. In this case, acrylic acid and/or salts thereof is preferably used as a main water-soluble ethylenically unsaturated monomer in an amount of 70 to 100 mol % based on the amount of all water-soluble ethylenically unsaturated monomers.

The water-soluble ethylenically unsaturated monomer is preferably dispersed in a state of an aqueous solution in a hydrocarbon dispersion medium, and then subjected to reversed phase suspension polymerization. When the water-soluble ethylenically unsaturated monomer is in the form of an aqueous solution, the dispersion efficiency in the hydrocarbon dispersion medium can be increased. The concentration of the water-soluble ethylenically unsaturated monomer in the aqueous solution is preferably in the range of 20% by mass to not more than the saturation concentration. In addition, from the viewpoint of easily obtaining the water absorption characteristics of the present invention, the concentration of the water-soluble ethylenically unsaturated monomer is more preferably 38% by mass or more, still more preferably 40% by mass or more, and further preferably 42% by mass or more. On the other hand, the concentration of the water-soluble ethylenically unsaturated monomer is more preferably 55% by mass or less, still more preferably 50% by mass or less, and further preferably 46% by mass or less.

When the water-soluble ethylenically unsaturated monomer has an acid group such as (meth)acrylic acid or 2-(meth) acrylamido-2-methylpropanesulfonic acid, the acid group may be neutralized with an alkaline neutralizing agent, as required, before use. Examples of such alkaline neutralizing agents include alkali metal salts such as sodium hydroxide, sodium carbonate, sodium hydrogen carbonate, potassium hydroxide, and potassium carbonate; and ammonia. These alkaline neutralizing agents may be used in the form of aqueous solutions to facilitate the neutralization operation. The above-mentioned alkaline neutralizing agents may be used alone or in combination of two or more.

The degree of neutralization of the water-soluble ethylenically unsaturated monomer with an alkaline neutralizing agent, calculated as the degree of neutralization with respect to all acid groups of the water-soluble ethylenically unsaturated monomer, is preferably 10 to 100 mol %, more preferably 30 to 90 mol %, still more preferably 40 to 85 mol %, and further preferably 50 to 80 mol %.

[Radical Polymerization Initiator]

Examples of the radical polymerization initiator added in the polymerization step include persulfates such as potassium persulfate, ammonium persulfate, and sodium persulfate, peroxides such as methyl ethyl ketone peroxide, methyl isobutyl ketone peroxide, di-t-butyl peroxide, t-butyl cumyl peroxide, t-butyl peroxyacetate, t-butyl peroxyisobutyrate, t-butyl peroxypivalate, and hydrogen peroxide, 2,2'-azobis (2-amidinopropane) dihydrochloride, 2,2'-azobis[2-(N-phenylamidino)propane]dihydrochloride, 2,2'-azobis[2-(N-allylamidino)propane] dihydrochloride, and 2,2'-azobis{2-[1-(2-hydroxyethyl)-2-imidazolin-2-yl]propane dihydrochloride, and azo compounds such as 2,2'-azobis{2-methyl-N-[1,1-bis(hydroxymethyl)-2-hydroxyethyl]propionamide}, 2,2'-azobis[2-methyl-N-(2-hydroxyethyl)-propionamide], and 4,4'-azobis(4-cyanovaleric acid). Among these radical polymerization initiators, potassium persulfate, ammonium persulfate, sodium persulfate, and 2,2'-azobis(2-amidinopropane) dihydrochloride are preferable from the viewpoint of easy availability and easy handling. These radical polymerization initiators may be used alone or in combination of two or more. The above-mentioned radical polymerization initiators may also be used in combination with reducing agents such as sodium sulfite, sodium hydrogensulfite, ferrous sulfate, and L-ascorbic acid to be used as redox polymerization initiators.

From the viewpoint of obtaining a water-absorbent resin that more suitably exhibits the effect of the present invention, the radical polymerization initiator to be mixed in the polymerization step preferably includes an azo compound and a peroxide. The molar ratio of the peroxide to the azo compound (peroxide/azo compound) is preferably in the range of 0.1 to 1.0, more preferably in the range of 0.2 to 0.8, and still more preferably in the range of 0.3 to 0.6.

The amount of the radical polymerization initiator to be used is, for example, 0.00005 to 0.01 mol per mole of the water-soluble ethylenically unsaturated monomer. When such a use amount is satisfied, the occurrence of an abrupt polymerization reaction can be avoided, and the polymerization reaction can be completed in an appropriate time.

[Internal Crosslinking Agent]

Examples of the internal crosslinking agent include those that can crosslink the polymer of the water-soluble ethylenically unsaturated monomer to be used, for example, unsaturated polyesters obtained by reacting polyols such as diols and triols, e.g., (poly)ethylene glycol, (poly)propylene glycol, 1,4-butanediol, trimethylolpropane, and (poly)glycerin, with unsaturated acids such as (meth)acrylic acid, maleic acid, and fumaric acid; bisacrylamides such as N,N-methylenebisacrylamide; di or tri(meth)acrylic acid esters obtained by reacting polyepoxides with (meth)acrylic acid; carbamyl di(meth)acrylates obtained by reacting polyisocyanates such as tolylene diisocyanate and hexamethylene diisocyanate with hydroxyethyl (meth)acrylate; compounds having two or more polymerizable unsaturated groups such as allylated starch, allylated cellulose, diallyl phthalate, N,N',N"-triallylisocyanurate, and divinylbenzene; polyglycidyl compounds such as diglycidyl compounds and triglycidyl compounds, e.g., (poly)ethylene glycol diglycidyl ether, (poly)propylene glycol diglycidyl ether, and (poly) glycerin diglycidyl ether; epihalohydrin compounds such as epichlorohydrin, epibromohydrin, and α-methylepichlorohydrin; compounds having two or more reactive functional groups such as isocyanate compounds, e.g., 2,4-tolylene diisocyanate and hexamethylene diisocyanate; and oxetane compounds such as 3-methyl-3-oxetanemethanol, 3-ethyl-3-oxetanemethanol, 3-butyl-3-oxetanemethanol, 3-methyl-3-oxetaneethanol, 3-ethyl-3-oxetaneethanol, and 3-butyl-3-oxetaneethanol. Among these internal crosslinking agents, unsaturated polyesters or polyglycidyl compounds are preferably used, diglycidyl ether compounds are more preferably used, and (poly)ethylene glycol diglycidyl ether, (poly) propylene glycol diglycidyl ether, and (poly)glycerin diglycidyl ether are still more preferably used. These internal crosslinking agents may be used alone or in combination of two or more.

The amount of the internal crosslinking agent to be used is preferably 0.02 mol or less, more preferably 0.000001 to 0.01 mol, still more preferably 0.00001 to 0.005 mol, and further preferably 0.00005 to 0.002 mol, per mole of the water-soluble ethylenically unsaturated monomer.

[Hydrocarbon Dispersion Medium]

Examples of the hydrocarbon dispersion medium include aliphatic hydrocarbons having 6 to 8 carbon atoms such as n-hexane, n-heptane, 2-methylhexane, 3-methylhexane, 2,3-dimethylpentane, 3-ethylpentane, and n-octane; alicyclic hydrocarbons such as cyclohexane, methylcyclohexane, cyclopentane, methylcyclopentane, trans-1,2-dimethylcyclopentane, cis-1,3-dimethylcyclopentane, and trans-1,3-dimethylcyclopentane; and aromatic hydrocarbons such as benzene, toluene, and xylene. Among these hydrocarbon dispersion media, n-hexane, n-heptane, and cyclohexane are suitably used especially in terms of being industrially readily available, stable in quality, and inexpensive. These hydrocarbon dispersion media may be used alone or in combination of two or more. As examples of mixtures of hydrocarbon dispersion media, the use of commercially available products such as Exxsol Heptane (produced by ExxonMobil Corporation; containing 75 to 85% by mass of heptane and its isomeric hydrocarbons) also leads to favorable results.

The amount of the hydrocarbon dispersion medium to be used is preferably 100 to 1500 parts by mass, and more preferably 200 to 1400 parts by mass per 100 parts by mass of the first-stage water-soluble ethylenically unsaturated monomer from the viewpoint of uniformly dispersing the water-soluble ethylenically unsaturated monomer, and facilitating control of the polymerization temperature. As described below, reversed phase suspension polymerization is carried out in a single stage or two or more multiple stages. The first-stage polymerization as mentioned above refers to the first-stage polymerization reaction in single-stage polymerization or multi-stage polymerization (the same applies hereinbelow).

[Dispersion Stabilizer]

(Surfactant)

In the reversed phase suspension polymerization, a dispersion stabilizer may be used to improve the dispersion stability of the water-soluble ethylenically unsaturated monomer in the hydrocarbon dispersion medium. As the dispersion stabilizer, a surfactant may be used.

Examples of surfactants which can be used include sucrose fatty acid esters, polyglycerin fatty acid esters, sorbitan fatty acid esters, polyoxyethylene sorbitan fatty acid esters, polyoxyethylene glycerin fatty acid esters, sorbitol fatty acid esters, polyoxyethylene sorbitol fatty acid esters, polyoxyethylene alkyl ethers, polyoxyethylene alkyl phenyl ethers, polyoxyethylene castor oil, polyoxyethylene hydrogenated castor oil, alkyl allyl formaldehyde condensate polyoxyethylene ethers, polyoxyethylene-polyoxypropylene block copolymers, polyoxyethylene polyoxypropyl alkyl ethers, polyethylene glycol fatty acid esters, alkyl glucosides, N-alkyl glyconamides, polyoxyethylene fatty acid amides, polyoxyethylene alkylamines, polyoxyethylene alkyl ether phosphates, and polyoxyethylene alkyl allyl ether phosphates. Among these surfactants, it is particularly preferable to use a sorbitan fatty acid ester, a polyglycerin fatty acid ester, or a sucrose fatty acid ester from the viewpoint of dispersion stability of the monomer. These surfactants may be used alone or in combination of two or more.

The amount of the surfactant to be used is preferably 0.1 to 30 parts by mass, and more preferably 0.3 to 20 parts by mass per 100 parts by mass of the first-stage water-soluble ethylenically unsaturated monomer.

(Polymeric Dispersion Agent)

As the dispersion stabilizer to be used in the reversed phase suspension polymerization, a polymeric dispersion agent may be used together with the surfactant described above.

Examples of the polymeric dispersion agent include maleic anhydride-modified polyethylene, maleic anhydride-modified polypropylene, maleic anhydride-modified ethylene-propylene copolymers, maleic anhydride-modified EPDM (ethylene-propylene-diene terpolymers), maleic anhydride-modified polybutadiene, maleic anhydride-ethylene copolymers, maleic anhydride-propylene copolymers, maleic anhydride-ethylene-propylene copolymers, maleic anhydride-butadiene copolymers, polyethylene, polypropylene, ethylene-propylene copolymers, oxidized polyethylene, oxidized polypropylene, oxidized ethylene-propylene copolymers, ethylene-acrylic acid copolymers, ethyl cellulose, and ethyl hydroxyethyl cellulose. Among these polymeric dispersion agents, maleic anhydride-modified polyethylene, maleic anhydride-modified polypropylene, maleic anhydride-modified ethylene-propylene copolymers, maleic anhydride-ethylene copolymers, maleic anhydride-propylene copolymers, maleic anhydride-ethylene-propylene copolymers, polyethylene, polypropylene, ethylene-propylene copolymers, oxidized polyethylene, oxidized polypropylene, and oxidized ethylene-propylene copolymers are particularly preferably used, from the viewpoint of dispersion stability of the monomer. These polymeric dispersion agents may be used alone or in combination of two or more.

The amount of the polymeric dispersion agent to be used is preferably 0.1 to 30 parts by mass, and more preferably 0.3 to 20 parts by mass, per 100 parts by mass of the first-stage water-soluble ethylenically unsaturated monomer.

[Other Components]

In the method for producing a water-absorbent resin, reversed phase suspension polymerization may be performed, if desired, with the addition of other components to the aqueous solution of the water-soluble ethylenically unsaturated monomer. As such other components, various additives such as a thickener and a chain transfer agent may be added.

As one example, reversed phase suspension polymerization may be performed with the addition of a thickener to the aqueous solution containing the water-soluble ethylenically unsaturated monomer. Adjusting the viscosity of the aqueous solution by adding a thickener in this manner makes it possible to control the median particle diameter attained in the reversed phase suspension polymerization.

As the thickener, for example, hydroxyethylcellulose, hydroxypropylcellulose, methylcellulose, carboxymethylcellulose, polyacrylic acid, (partially) neutralized polyacrylic acid, polyethylene glycol, polyacrylamide, polyethyleneimine, dextrin, sodium alginate, polyvinyl alcohol, polyvinylpyrrolidone, and polyethylene oxide can be used. With a fixed stirring speed during the polymerization, the higher the viscosity of the aqueous solution of the water-soluble ethylenically unsaturated monomer, the larger primary particles and/or secondary particles of the resulting particles tend to be.

[Reversed Phase Suspension Polymerization]

In performing the reversed phase suspension polymerization, for example, an aqueous monomer solution containing a water-soluble ethylenically unsaturated monomer is dispersed in a hydrocarbon dispersion medium in the presence of a dispersion stabilizer. In this case, the timing of the addition of the dispersion stabilizer (surfactant or polymeric dispersion agent) may be either before or after the addition of the aqueous monomer solution as long as it is before starting the polymerization reaction.

In particular, from the viewpoint of easily reducing the amount of the hydrocarbon dispersion medium remaining in the resulting water-absorbent resin, it is preferable to perform polymerization after dispersing the aqueous monomer solution in the hydrocarbon dispersion medium in which the polymeric dispersion agent is dispersed and then further dispersing the surfactant.

Such reversed phase suspension polymerization can be carried out in one stage or in two or more multiple stages. From the viewpoint of enhancing productivity, it is preferable to perform the polymerization in two or three stages.

When the reversed phase suspension polymerization is performed in two or more multiple stages, it can be carried out by performing the first-stage reversed phase suspension polymerization, subsequently adding a water-soluble ethylenically unsaturated monomer to the reaction mixture obtained through the first-stage polymerization reaction and mixing the resulting mixture, and then performing the reversed phase suspension polymerization in the second and subsequent stages in the same manner as in the first stage. In the reversed phase suspension polymerization in each of the second and subsequent stages, reversed phase suspension polymerization can be performed with addition of a radical polymerization initiator and, as necessary, an internal crosslinking agent in addition to a water-soluble ethylenically unsaturated monomer in amounts within the above-described molar ratio ranges of the respective components with respect to the water-soluble ethylenically unsaturated monomer based on the amount of the water-soluble ethylenically unsaturated monomer to be added at the time of the reversed phase suspension polymerization in each of the second and subsequent stages. The amount of the water-soluble ethylenically unsaturated monomer and the ratios of the polymerization initiator, the internal crosslinking agent, and the like to the water-soluble ethylenically unsaturated monomer may be the same or different among the first stage and the second and subsequent stages as long as they are within the above ranges.

The reaction temperature of the polymerization reaction is preferably 20 to 110° C., and more preferably 40 to 90° C. from the viewpoint of allowing the polymerization to proceed quickly to reduce the polymerization time for improved economic efficiency, and readily removing the heat of polymerization to perform a smooth reaction.

<Post-Crosslinking Step>

Next, the water-absorbent resin is obtained by adding a post-crosslinking agent to the hydrous gel having an internally crosslinked structure which has been obtained by polymerizing the water-soluble ethylenically unsaturated monomer, and crosslinking the hydrous gel (post-crosslinking reaction). This post-crosslinking reaction is performed in the presence of a post-crosslinking agent after polymerization of a water-soluble ethylenically unsaturated monomer. By performing such a post-crosslinking reaction, it is possible to appropriately increase the crosslinking density in the vicinity of the surface of a water-absorbent resin and obtain a water-absorbent resin having various improved performances such as water retention capacity, water absorption capacity under a load and non-pressurization DW.

Examples of the post-crosslinking agent include compounds having two or more reactive functional groups. Examples thereof include polyols such as ethylene glycol, propylene glycol, 1,4-butanediol, trimethylolpropane, glycerin, polyoxyethylene glycol, polyoxypropylene glycol, and polyglycerin; polyglycidyl compounds such as (poly)ethylene glycol diglycidyl ether, (poly)glycerin diglycidyl ether, (poly)glycerin triglycidyl ether, trimethylolpropane triglycidyl ether, (poly)propylene glycol polyglycidyl ether, and (poly)glycerol polyglycidyl ether; haloepoxy compounds such as epichlorohydrin, epibromohydrin, and α-methylepichlorohydrin; isocyanate compounds such as 2,4-tolylene diisocyanate and hexamethylene diisocyanate; oxetane compounds such as 3-methyl-3-oxetanemethanol, 3-ethyl-3-oxetanemethanol, 3-butyl-3-oxetanemethanol, 3-methyl-3-oxetaneethanol, 3-ethyl-3-oxetaneethanol, and 3-butyl-3-oxetaneethanol; oxazoline compounds such as 1,2-ethylenebisoxazoline; carbonate compounds such as ethylene carbonate; and hydroxyalkylamide compounds such as bis[N,N-di(β-hydroxyethyl)]adipamide. Among these post-crosslinking agents, polyglycidyl compounds such as (poly)ethylene glycol diglycidyl ether, (poly)glycerin diglycidyl ether, (poly)glycerin triglycidyl ether, trimethylolpropane triglycidyl ether, (poly)propylene glycol polyglycidyl ether, and (poly)glycerol polyglycidyl ether are preferred. These post-crosslinking agents may be used alone or in combination of two or more.

The amount of the post-crosslinking agent to be used is preferably 0.00001 to 0.01 mol, more preferably 0.00005 to 0.005 mol, and still more preferably 0.0001 to 0.001 mol per mole of all the water-soluble ethylenically unsaturated monomer used in the polymerization.

As a method of adding the post-crosslinking agent, the post-crosslinking agent may be added either as it is or in the form of an aqueous solution, and as necessary, it may be added in the form of a solution prepared using a hydrophilic organic solvent as a solvent. Examples of the hydrophilic organic solvent include lower alcohols such as methyl alcohol, ethyl alcohol, n-propyl alcohol, and isopropyl alcohol; ketones such as acetone and methyl ethyl ketone; ethers such as diethyl ether, dioxane, and tetrahydrofuran; amides such as N,N-dimethylformamide; and sulfoxides such as dimethyl sulfoxide. These hydrophilic organic solvents may be used alone, in combination of two or more, or in the form of a mixed solvent with water.

The timing of the addition of the post-crosslinking agent may be any time after the polymerization of the water-soluble ethylenically unsaturated monomer, and it is preferable to add the post-crosslinking agent in the presence of 5 to 140 parts by mass of water per 100 parts by mass of the water-soluble ethylenically unsaturated monomer, more preferably added in the presence of 15 to 100 parts by mass of water, still more preferably added in the presence of 20 to 50 parts by mass of water, and even more preferably added in the presence of 22 to 28 parts by mass of water. The amount of water herein refers to the total amount of the water contained in the reaction system and the water that is used, as required, during the addition of the post-crosslinking agent. When the post-crosslinking agent is added in a state in which the amount of water is higher than 140 parts by mass, the water retention capacity tends to decrease. In addition, when the post-crosslinking agent is added in a state in which the amount of water is less than 5 parts by mass, the reaction of the post-crosslinking agent tends to be insufficient.

The reaction temperature during the post-crosslinking reaction is preferably 50 to 250° C., more preferably 60 to 180° C., still more preferably 60 to 140° C., and further preferably 70 to 120° C. The reaction time of the post-crosslinking reaction is preferably 1 to 300 minutes, and more preferably 5 to 200 minutes.

<Drying Step>

The method may include a drying step of removing water, a hydrocarbon dispersion medium, and the like by distillation by externally applying energy such as heat after performing the reversed phase suspension polymerization described above. When dehydration from the hydrous gel after the reversed phase suspension polymerization is performed, the system in which the hydrous gel is dispersed in the hydrocarbon dispersion medium is heated, so that water and the hydrocarbon dispersion medium are temporarily distilled off to the outside of the system by azeotropic distillation. At this time, returning only the removed hydrocarbon dispersion medium into the system permits continuous azeotropic distillation. This embodiment is preferable from the viewpoint that the resin is hardly degraded because the temperature in the system during drying is maintained at or below the azeotropic temperature with the hydrocarbon dispersion medium. Subsequently, water and the hydrocarbon dispersion medium are distilled off, and thus a water-absorbent resin is obtained. By controlling the processing conditions in this drying step after the polymerization and thereby adjusting the amount of dehydration, it is possible to control various performances of the resulting water-absorbent resin.

In the drying step, the drying treatment by distillation may be performed either under normal pressure or under reduced pressure. From the viewpoint of increasing the drying efficiency, the drying treatment may be performed under a flow of gas such as nitrogen. When the drying treatment is performed under normal pressure, the drying temperature is preferably 70 to 250° C., more preferably 80 to 180° C., still more preferably 80 to 140° C., and further preferably 90 to 130° C. In the case where the drying treatment is performed under reduced pressure, the drying temperature is preferably 40 to 160° C., and more preferably 50 to 110° C.

When the post-crosslinking step using the post-crosslinking agent is performed, the above-described drying step by distillation is performed after the completion of the post-crosslinking step. Alternatively, the post-crosslinking step and the drying step may be performed simultaneously.

The water-absorbent resin may contain an additive according to the purpose. Examples of such additives include inorganic powders, surfactants, oxidants, reducing agents, metal chelating agents, radical chain inhibitors, antioxidants, and antibacterial agents. For example, by adding 0.05 to 5 parts by mass of amorphous silica as an inorganic powder to 100 parts by mass of the water-absorbent resin, the flowability of the water-absorbent resin can be further improved.

EXAMPLES

The present invention will be hereinafter described in detail by way of examples and comparative examples. It, however, is to be noted that the present invention is not limited to the examples.

The water-absorbent resins obtained in Examples and Comparative Examples were evaluated by the following tests. Unless otherwise specified, the measurement was performed under an environment of a temperature of 25±2° C. and a humidity of 50±10%. Hereinafter, each evaluation test method will be described.

<Physiological Saline Retention Capacity>

A cotton bag (Cottonbroad No. 60, 100 mm in width, 200 mm in length) in which 2.0 g of the water-absorbent resin particles had been weighed was placed in a 500-mL beaker. 500 g of a 0.9% by mass aqueous sodium chloride solution (physiological saline) was poured into the cotton bag containing the water-absorbent resin at a time such that no lumps were formed. Then, the top of the cotton bag was tied with a rubber band and the resultant was left at rest for 30 minutes, and thereby the water-absorbent resin was swollen. The cotton bag after 30 minutes lapse was dehydrated for one minute using a dehydrator (product number: H-122, manufactured by KOKUSAN Co., Ltd.) set at a centrifugal force of 167 G, and the mass Wa (g) of the dehydrated cotton bag containing the swollen gel was measured. The same operation was performed without adding a water-absorbent resin, and the empty mass Wb (g) of the cotton bag in a wet state was measured, and the physiological saline retention capacity was calculated from the following formula.

$$\text{Physiological saline retention capacity } [\text{g/g}] = [Wa - Wb]/2.0$$

<Physiological Saline Absorption Capacity Under a Load of 4.14 kPa>

Figure 2:
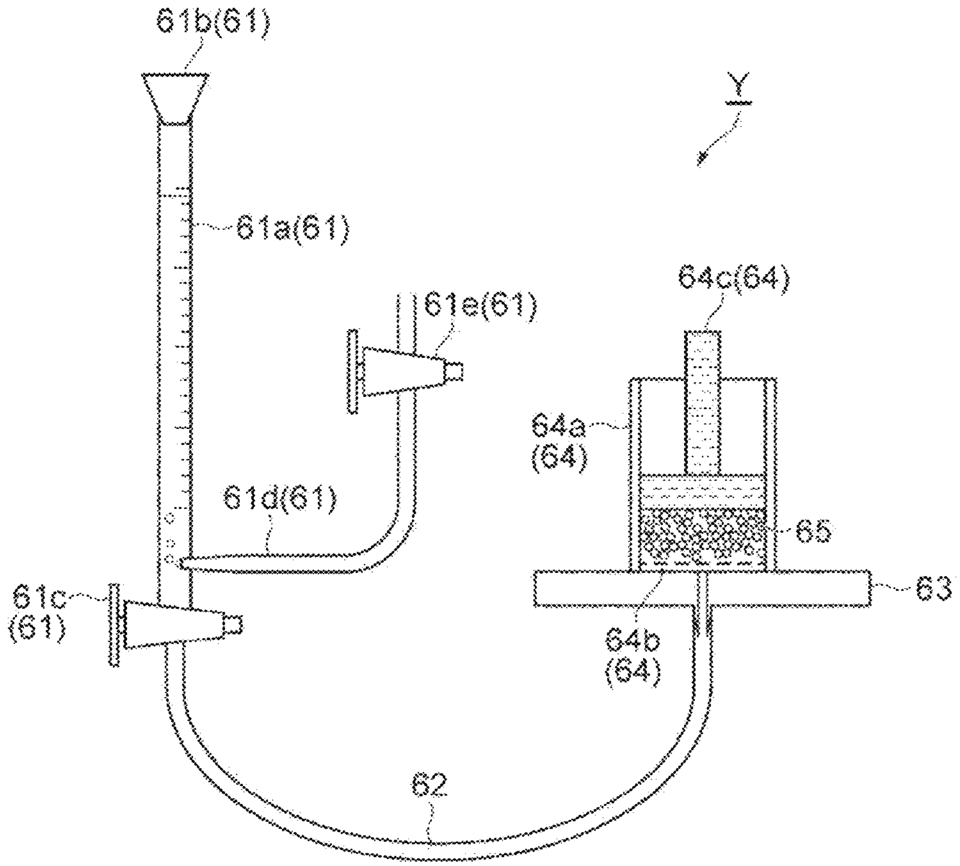
FIG. 2 is a schematic view of a measuring device to be used for measuring the physiological saline absorption capacity of a water-absorbent resin under a load of 4.14 kPa.

The physiological saline absorption capacity (room temperature, 25° C.±2° C.) under a load (under pressurization) of a water-absorbent resin particle was measured using a measuring device Y illustrated in FIG. 2. The measuring device Y is composed of a burette part 61, a conduit pipe 62, a measuring stand 63, and a measuring part 64 placed on the measuring stand 63. The burette part 61 includes a burette 61*a* extending in a vertical direction, a rubber stopper 61*b* disposed at an upper end of the burette 61*a*, a cock 61*c* disposed at a lower end of the burette 61*a*, an air introducing pipe 61*d* having one end extending to the burette 61*a* in the vicinity of the cock 61*c*, and a cock 61*e* disposed at the other end side of the air introducing pipe 61*d*. The conduit pipe 62 is attached between the burette part 61 and the measuring stand 63. The conduit pipe 62 has an inner diameter of 6 mm. There is a hole having a diameter of 2 mm in a center portion of the measuring stand 63, and the conduit pipe 62 is connected to the hole. The measuring part 64 includes a cylinder 64*a* (made of acrylic resin (PLEXIGLAS)), a nylon mesh 64*b* adhered to a bottom portion of the cylinder 64*a*, and a weight 64*c*. The cylinder 64*a* has an inner diameter of 20 mm. The nylon mesh 64*b* has a mesh size of 75 μm (200 mesh). At the time of measurement, water-absorbent resin particles 65 to be measured are uniformly scattered on the nylon mesh 64*b*. The weight 64*c* has a diameter of 19 mm, and the weight 64*c* has a mass of 120 g. The weight 64*c* is placed on the water-absorbent resin particles 65, and a load of 4.14 kPa can be applied to the water-absorbent resin particles 65.

0.100 g of the water-absorbent resin particles 65 was put into the cylinder 64*a* of the measuring device Y, then the weight 64*c* was placed thereon and the measurement was started. Because air of the same volume as that of the physiological saline absorbed by the water-absorbent resin particles 65 is quickly and smoothly supplied into the burette 61*a* through the air introducing pipe, a reduced amount in water level of the physiological saline in the burette 61*a* indicates an amount of the physiological saline absorbed by the water-absorbent resin particles 65. A scale of the burette 61*a* was engraved from 0 mL in increments of 0.5 mL from the top to bottom direction. A scale Va of the burette 61*a* before the start of water absorption and a scale Vb of the burette 61*a* 60 minutes after the start of water absorption were read as water levels of the physiological saline, and a physiological saline absorption capacity under a load of 4.14 kPa was calculated from the following formula.

$$\text{Physiological saline absorption capacity } [\text{mL/g}] \text{ under a load of } 4.14 \text{ kPa} = (Vb - Va)/0.100$$

<Value of Non-Pressurization DW (Demand Wettability) after 5 Minutes>

Figure 3:
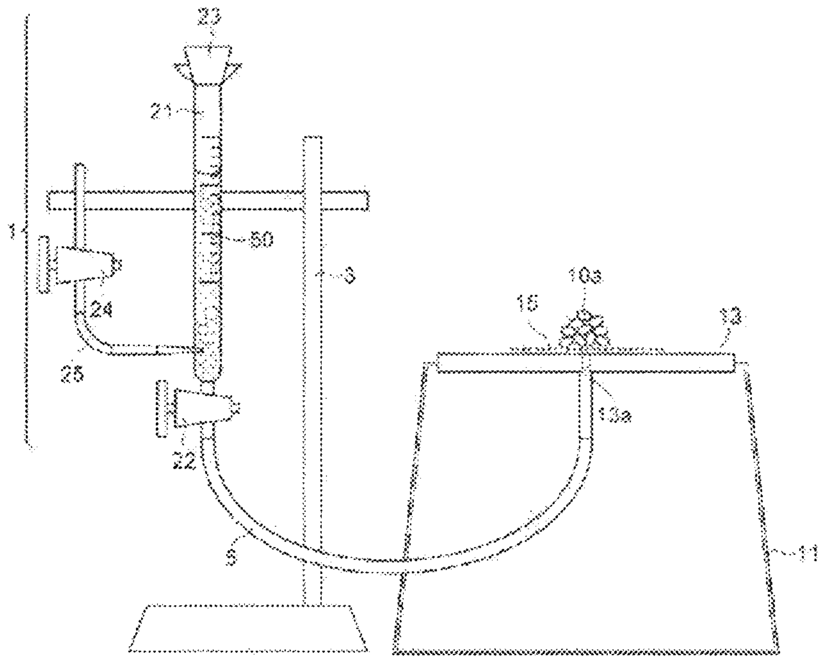
FIG. 3 is a schematic view of a measuring device to be used for measuring the non-pressurization DW of a water-absorbent resin.

The non-pressurization DW of particles of a water-absorbent resin was measured using a measuring device illustrated in FIG. 3. The measurement was carried out five times for one water-absorbent resin, and an average value of three measured values excluding a minimum value and a maximum value was determined. The measuring device has a burette part 1, a conduit pipe 5, a measuring stand 13, a nylon mesh sheet 15, a stand 11, and a clamp 3. The burette part 1 has a burette tube 21 on which a scale is engraved, a rubber stopper 23 for sealing an opening at an upper part of the burette tube 21, a cock 22 connected to a distal end of a lower part of the burette tube 21, an air introducing pipe 25 connected to the lower part of the burette tube 21, and a cock 24. The burette part 1 is fixed by the clamp 3. The flat plate-shaped measuring stand 13 has a through-hole 13*a* having a diameter of 2 mm and formed in the center portion of the measuring stand 13, and is supported by the height-variable stand 11. The through-hole 13*a* of the measuring stand 13 and the cock 22 of the burette part 1 are connected by the conduit pipe 5. The conduit pipe 5 has an inner diameter of 6 mm.

First, the cock 22 and the cock 24 of the burette part 1 were closed, and a 0.9% by mass saline solution 50 that had been adjusted to 25° C. was put into the burette tube 21 through the opening at the upper part of the burette tube 21. The concentration of 0.9% by mass of the saline solution is a concentration based on the mass of the saline solution. The opening of the burette tube 21 was sealed with the rubber stopper 23, and then the cock 22 and the cock 24 were opened. The inside of the conduit pipe 5 was filled with the 0.9% by mass saline solution 50 so as to prevent air bubbles from entering. The height of the measuring stand 13 was adjusted such that the height of a water surface of the 0.9% by mass saline solution having reached the inside of the through-hole 13*a* was the same as the height of an upper surface of the measuring stand 13. After the adjustment, the height of the water surface of the 0.9% by mass saline solution 50 in the burette tube 21 was read on the scale engraved on the burette tube 21, and this position was defined as a zero point (value read at 0 seconds).

The nylon mesh sheet 15 (100 mm×100 mm, 250 mesh, thickness: about 50 μm) was laid in the vicinity of the through-hole 13*a* on the measuring stand 13, and a cylinder having an inner diameter of 30 mm and a height of 20 mm was placed on the center portion of the nylon mesh sheet. 1.00 g of a water-absorbent resin 10*a* were uniformly scattered in the cylinder. Thereafter, the cylinder was carefully removed, affording a sample in which the water-absorbent resin 10*a* was dispersed in a circle shape in the center portion of the nylon mesh sheet 15. Subsequently, the nylon mesh sheet 15 on which the water-absorbent resin 10*a* was placed was moved rapidly to such an extent that the water-absorbent resin 10*a* was not dissipated such that the center of the nylon mesh sheet was located at the position of the through-hole 13*a*, and then the measurement was started. The time when air bubbles were first introduced from the air introducing pipe 25 into the burette tube 21 was defined as a start of water absorption (0 seconds).

A decrease amount of the 0.9% by mass saline solution 50 in the burette tube 21 (that is, an amount of the 0.9% by mass saline solution absorbed by the water-absorbent resin 10*a*) was sequentially read, and a decrease in weight We (g) of the 0.9% by mass saline solution 50 after 5 minutes from the start of the water absorption by the water-absorbent resin 10*a* was read. From the Wc, a value of non-pressurization DW after 5 minutes was determined by the following formula. The non-pressurization DW is a water absorption capacity per 1.00 g of the water-absorbent resin 10*a*.

$$\text{Value (mL/g) of non-pressurization } DW = Wc/1.00$$

<Median Particle Diameter>

10 g of water-absorbent resin particles were sieved using a continuous automated sonic sieving particle size analyzer (Robot Sifter RPS-205, manufactured by Seishin Enterprise Co., Ltd.), sieves with JIS standard mesh sizes of 850 μm, 710 μm, 600 μm, 500 μm, 425 μm, 300 μm, 250 μm, and 150 μm, and a receptacle. A mass of the particles remaining on each sieve was calculated as a mass percentage relative to the total amount. The mass percentage of the particles remaining on each sieve was integrated in a descending order of particle sizes, and the relationship between the mesh size and an integrated value of the mass percentage of particles remaining on the sieve was plotted on a logarithmic probability paper. The plotted points on the probability paper were connected by straight lines, and thereby a particle diameter corresponding to 50% by mass of the integrated mass percentage was determined and taken as a median particle diameter.

<Preparation of Test Solution>

A test solution was prepared by blending and dissolving components in ion-exchanged water such that inorganic salts were present as shown below, and further blending a small amount of Blue No. 1.

Composition of Test Solution

| | |
|---|---|
| Deionized water | 5919.6 g |
| NaCl | 60.0 g |
| $CaCl_2 \cdot H_2O$ | 1.8 g |
| $MgCl_2 \cdot 6H_2O$ | 3.6 g |
| Food Blue No. 1 (for coloring) | |
| 1% - Triton X-100 | 15.0 g |

<Permeation Time>

In a room having the temperature of 25±2° C., an absorbent article was placed on a horizontal table. Next, a 200-mL liquid charging cylinder (cylinder opened at both ends) having a charging port with an inner diameter of 3 cm was placed at the center of the main surface of the absorbent article. Subsequently, 150 mL of a test solution adjusted to 25±1° C. was charged into the cylinder at one time. Using a stopwatch, the time taken until the test solution completely disappeared from the inside of the cylinder was measured and the time was obtained as a permeation time [sec]. The results are shown in Tables 2, 3 and 4.

<Leakage Test (Slope Absorption Test)>

Figure 4:
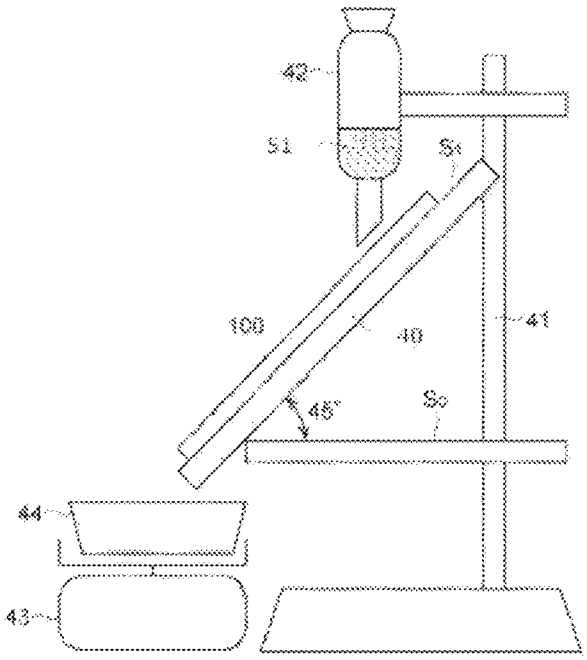
FIG. 4 is a schematic view for explaining the method of a leakage test (slope absorption test) of an absorbent article.

FIG. 4 is a schematic diagram illustrating a method of evaluating the leakage property of an absorbent article. A support plate 40 (an acrylic resin plate was used here; hereinafter also referred to as an inclined plane $S_1$) with a length of 45 cm and having a flat main surface was fixed by a stand 41 in a state of being inclined at 45±1 degrees with respect to a horizontal plane $S_0$. An absorbent article 100 for testing was bonded onto the inclined plane $S_1$ of the fixed support plate 40 such that a longitudinal direction of the absorbent article was along a longitudinal direction of the support plate 40. Next, a test solution 51 adjusted to 25±1° C. was dropped from a dropping funnel 42 disposed vertically above the absorbent article toward a position 8 cm, in an upper direction, from the center of an absorber in the absorbent article 100. 80 mL of the test solution was dropped per one time at a rate of 8 mL/sec. The distance between the tip of the dropping funnel 42 and the absorbent article was 10±1 mm. The test solution was repeatedly added under the same conditions at intervals of 10 minutes from the start of the first addition of the test solution, and the test solution was added. The test solution was added until leakage was observed, and the number of the addition was defined as the number of addition until the occurrence of leakage.

In a case where the test solution that was not absorbed by the absorbent article 100 leaked out from a lower part of the support plate 40, the leaked test solution was recovered in a metal tray 44 disposed below the support plate 40. The mass (g) of the recovered test solution was measured with a balance 43, and the value was recorded as the amount of leakage. The amount of leakage was subtracted from a total amount of the test solution added to calculate an amount of absorption until the leakage occurred. As this numerical value is larger, it is determined that leakage of liquid is less likely to occur when the absorbent article is worn. The density of the test solution was set to 1.0 g/mL. The results are shown in Tables 2, 3 and 4.

<Production of Water-Absorbent Resin>

Production Example 1

A round-bottomed cylindrical separable flask having the inner diameter of 11 cm and an internal volume of 2 L, equipped with a reflux condenser, a dropping funnel, a nitrogen gas introduction tube, and a stirrer was prepared. As the stirrer, one having a stirring blade having two stages of four inclined paddle blades with a blade diameter of 5 cm was used. The flask was charged with 264 g of n-heptane as a hydrocarbon dispersion medium and 0.736 g of a maleic anhydride-modified ethylene-propylene copolymer (Hi-WAX 1105A available from Mitsui Chemicals, Inc.) as a dispersion agent, which were then mixed. While the mixture in the flask was stirred at a rotation speed of a stirrer of 300 rpm, the temperature was raised to 80° C. to dissolve the dispersion agent in n-heptane. The solution formed was cooled to 50° C. 92.0 g (1.03 mol) of an 80.5% by mass aqueous solution of acrylic acid as a water-soluble ethylenically unsaturated monomer was placed in a beaker having an internal volume of 300 mL, and 102.8 g of a 30% by mass aqueous solution of sodium hydroxide was added dropwise into the beaker with external cooling to perform 75 mol % neutralization. Thereafter, 0.092 g of hydroxyethylcellulose (HEC AW-15F available from Sumitomo Seika Chemicals Co. Ltd.) as a thickener, 0.0920 g (0.339 mmol) of 2,2'-azobis(2-amidinopropane) dihydrochloride as an azo compound, 0.0276 g (0.102 mmol) of potassium persulfate as a peroxide, 0.00460 g (0.0264 mmol) of ethylene glycol diglycidyl ether as an internal crosslinking agent, and 8.28 g of ion-exchanged water were added and dissolved. As a result, a first-stage aqueous monomer solution was prepared.

The first-stage aqueous monomer solution prepared was added to the n-heptane solution containing the dispersion agent in the separable flask and stirred for 10 minutes. Next, a surfactant solution prepared by dissolving 0.736 g of sucrose stearate (HLB: 3, Mitsubishi-Kagaku Foods Corporation, Ryoto Sugar Ester S-370) as a surfactant in 6.62 g of n-heptane by heating was further added to the reaction solution, and the inside of the system was sufficiently replaced with nitrogen while stirring at a rotation speed of the stirrer of 600 rpm. Thereafter, the flask was soaked in a water bath at 70° C. to raise the temperature, and polymerization was performed for 60 minutes. Thereby, a first-stage polymerization slurry was obtained.

Next, 128.8 g (1.44 mol) of an 80.5% by mass aqueous solution of acrylic acid as an ethylenically unsaturated monomer was placed in another beaker having an internal volume of 500 ml, and 143.89 g of a 30% by mass aqueous solution of sodium hydroxide was added dropwise thereto with external cooling to perform 75 mol % neutralization. Thereafter, 0.129 g (0.475 mmol) of 2,2'-azobis(2-amidinopropane) dihydrochloride as an azo compound, 0.0386 g (0.143 mmol) of potassium persulfate as a peroxide, 0.0116 g (0.0665 mmol) of ethylene glycol diglycidyl ether as an internal crosslinking agent, and 11.2 g of ion-exchanged water were added thereto and dissolved. Thereby, a second-stage aqueous monomer solution was prepared.

The inside of the separable flask system was cooled to 25° C. with stirring at a rotation speed of the stirrer of 1000 rpm. Then, the whole amount of the second-stage aqueous monomer solution was added to the first-stage polymerization slurry in the separable flask, and the inside of the system was replaced with nitrogen for 30 minutes. Thereafter, the flask was soaked in the water bath at 70° C. again to raise the temperature, and a polymerization reaction was performed for 60 minutes.

To the reaction solution containing hydrous gel polymer resulting from the second-stage polymerization was added with stirring 0.265 g of a 45% by mass aqueous solution of pentasodium diethylenetriamine pentaacetate. Then, the flask was soaked in an oil bath set at 125° C., and 231.3 g of water was removed out of the system by azeotropic distillation of water and n-heptane. Then, 4.42 g (0.507 mmol) of a 2% by mass aqueous ethylene glycol diglycidyl ether solution was added to the flask, and the temperature inside the separable flask was kept at 83° C. for 2 hours.

Thereafter, the separable flask was soaked in an oil bath set at 125° C. and n-heptane was removed, affording polymer particles (dry product). The polymer particles were passed through a sieve with a mesh size of 850 μm, and 0.2% by mass, based on the mass of the polymer particles, of amorphous silica (available from Oriental Silicas Corporation, TOKUSIL NP-S, hydrophilic) was mixed with the polymer particles, affording 220.2 g of water-absorbent resin particles containing the amorphous silica. The performance of the water-absorbent resin particles is shown in Table 1.

Production Example 2

228.0 g of water-absorbent resin particles were obtained in the same manner as in Production Example 1 except that the amount of n-heptane to be used as a hydrocarbon dispersion medium was changed to 293 g, the amount of ion-exchanged water to be dissolved in the first-stage aqueous monomer solution was changed to 39.9 g, in the preparation of the first-stage aqueous monomer solution, the amount of potassium persulfate as a radical polymerization agent was changed to 0.0736 g (0.272 mmol), the azo compound 2,2'-azobis(2-amidinopropane) dihydrochloride was not added, the amount of ethylene glycol diglycidyl ether as an internal crosslinking agent was changed to 0.0101 g (0.0581 mmol), in the preparation of the second-stage aqueous monomer solution, the amount of potassium persulfate as a radical polymerization agent was changed to 0.103 g (0.381 mmol), the amount of the azo compound 2,2'-azobis(2-amidinopropane) dihydrochloride was not added, the amount of water to be removed out of the system by azeotropic distillation was changed to 247.9 g, and the mixing amount of amorphous silica with respect to polymer particles (dry product) was changed to 0.5% by mass. The performance of the water-absorbent resin particles is shown in Table 1.

Production Example 3

224.6 g of water-absorbent resin particles were obtained in the same manner as in Production Example 2 except that the amount of ion-exchanged water to be dissolved in the first-stage aqueous monomer solution was changed to 40.7 g, the amount of ethylene glycol diglycidyl ether as an internal crosslinking agent was changed to 0.00276 g (0.0158 mmol), and the amount of water to be removed out of the system by azeotropic distillation was changed to 266.9 g. The performance of the water-absorbent resin particles is shown in Table 1.

Production Example 4

229.0 g of water-absorbent resin particles were obtained in the same manner as in Production Example 1 except that the amount of n-heptane to be used as a hydrocarbon dispersion medium was changed to 293 g, the amount of ion-exchanged water to be dissolved in the first-stage aqueous monomer solution was changed to 40.9 g, the rotation speed during the first-stage polymerization was changed to 550 rpm, and the amount of water to be removed out of the system by azeotropic distillation was changed to 234.2 g. The performance of the water-absorbent resin particles is shown in Table 1.

<Production of Absorbent Article>

Example 1

Using an air flow mixer (Pad former manufactured by Autec Ltd.), 7.7 g of the water-absorbent resin particles obtained in Production Example 1 and 7.7 g of pulverized pulp were uniformly mixed by air papermaking to prepare a sheet-shaped absorber having a size of 32 cm×12 cm. Then, both surfaces of the absorber were covered with a hydrophilic spunbonded nonwoven fabric (manufactured by TORAY POLYTECH NANTONG, basis weight: 17 g/m$^2$, size: 37 cm×30 cm) as a core wrap sheet. Specifically, the 37 cm side of the core wrap sheet was aligned with the longitudinal direction of the absorber, the core wrap sheet was disposed on the absorber such that the central portion of the absorber was positioned just on the central portion of the core wrap sheet. Then, both end edge portions of the core wrap sheet in the lateral direction were folded back to the lower portion side of the absorber, and both the end edge portions were overlapped. A load of 196 kPa was applied to the core-wrapped absorber for 30 seconds, and then thermally fused regions each having a width of about 5 mm were formed at both ends in the longitudinal direction of the core wrap using a heat sealer (Fuji Impulse Co., Ltd., FI-450-5, time setting: 3 to 5). A hydrophilic air-through nonwoven fabric (manufactured by Rengo Nonwoven Products Co., Ltd., basis weight: 17 g/m$^2$, size: 32 cm×12 cm) was disposed on the upper surface of the core-wrapped absorber, and a polyethylene liquid-impermeable sheet having the same size and a basis weight of 40 g/m$^2$ was disposed on the lower surface of the absorber. Thereby, an absorbent article for testing was prepared. In the absorbent article, the basis weight of the water-absorbent resin particles was 200 g/m$^2$, and the basis weight of the pulverized pulp (hydrophilic fiber) was 200 g/m$^2$. The mass of the absorbent article was 19.0 g.

Comparative Example 1

An absorbent article of Comparative Example 1 was prepared in the same manner as in Example 1 except that the water-absorbent resin particles were changed to the water-absorbent resin particles obtained in Production Example 2.

Comparative Example 2

An absorbent article of Comparative Example 2 was prepared in the same manner as in Example 1 except that the water-absorbent resin particles were changed to the water-absorbent resin particles obtained in Production Example 3.

Comparative Example 3

An absorbent article of Comparative Example 3 was prepared in the same manner as in Example 1 except that the water-absorbent resin particles were changed to the water-absorbent resin particles obtained in Production Example 4.

Example 2

An absorbent article of Example 2 was prepared in the same manner as in Example 1 except that a wire mesh having a grid size of 1.0 cm×1.0 cm was placed on the skin-facing surface of the absorber covered with the core wrap sheet, a load of 196 kPa was applied for 30 seconds, and the skin-facing surface of the absorber was embossed in a grid shape.

Comparative Example 4

An absorbent article of Comparative Example 4 was prepared in the same manner as in Example 2 except that the water-absorbent resin particles were changed to the water-absorbent resin particles obtained in Production Example 2.

Comparative Example 5

An absorbent article of Comparative Example 5 was prepared in the same manner as in Example 2 except that the water-absorbent resin particles were changed to the water-absorbent resin particles obtained in Production Example 3.

Comparative Example 6

An absorbent article of Comparative Example 6 was prepared in the same manner as in Example 2 except that the water-absorbent resin particles were changed to the water-absorbent resin particles obtained in Production Example 4.

Example 3

Both ends of the core wrap in the longitudinal direction were bonded together by heat sealing, and then a liquid-acquisition diffusion sheet was disposed on the skin-facing surface of the absorber. An absorbent article of Example 3 was prepared in the same manner as in Example 1 except that the liquid-acquisition diffusion sheet was a hydrophilic air-through nonwoven fabric (manufactured by Rengo Nonwoven Products Co., Ltd., basis weight: 20 g/m$^2$) having a size: 20 cm in the longitudinal direction of the absorber×10 cm in the lateral direction of the absorber, and the central portion of the liquid-acquisition diffusion sheet and the central portion of the skin-facing surface of the absorber were disposed to overlap each other.

Example 4

Both ends of the core wrap in the longitudinal direction were bonded together by heat sealing, and then a liquid-acquisition diffusion sheet was disposed on the skin-facing surface of the absorber. An absorbent article of Example 4 was prepared in the same manner as in Example 1 except that the liquid-acquisition diffusion sheet was a hydrophilic air-through nonwoven fabric (manufactured by KNH Enterprise Co., Ltd., basis weight: 50 g/m$^2$) having a size: 20 cm in the longitudinal direction of the absorber×10 cm in the lateral direction of the absorber, and the central portion of the liquid-acquisition diffusion sheet and the central portion of the skin-facing surface of the absorber were disposed to overlap each other.

Example 5

An absorbent article of Example 5 was prepared in the same manner as in Example 1 except that the central portion of the absorber had a region (slit portion) sized 10 cm in the longitudinal direction×1 cm in the lateral direction in which the water-absorbent resin particles and the pulverized pulp were not laminated; and a load of 196 kPa was applied for 30 seconds and then a core wrap sheet at the slit portion was applied with spray adhesive (Spray Adhesive 77 manufactured by 3M) and adhered.

Comparative Example 7

An absorbent article of Comparative Example 7 was prepared in the same manner as in Example 5 except that the water-absorbent resin particles were changed to the water-absorbent resin particles obtained in Production Example 2.

Comparative Example 8

An absorbent article of Comparative Example 8 was prepared in the same manner as in Example 5 except that the water-absorbent resin particles were changed to the water-absorbent resin particles obtained in Production Example 3.

Comparative Example 9

An absorbent article of Comparative Example 9 was prepared in the same manner as in Example 5 except that the water-absorbent resin particles were changed to the water-absorbent resin particles obtained in Production Example 4.

TABLE 1

| | Water-absorbent resin | | | |
|---|---|---|---|---|
| | Physiological saline retention capacity [g/g] | Water absorption capacity under a load of 4.14 kPa [ml/g] | Value of non-pressurization DW after 5 minutes [ml/g] | Median particle diameter [μm] |
| Production Example 1 | 48 | 17 | 64 | 375 |
| Production Example 2 | 35 | 25 | 55 | 361 |
| Production Example 3 | 49 | 9 | 61 | 341 |
| Production Example 4 | 49 | 18 | 36 | 348 |

TABLE 2

| | Absorbent article | | | | | | | |
|---|---|---|---|---|---|---|---|---|
| | Water-absorbent resin used | Means for improving liquid permeability | Permeation time (sec) | Leakage test Number of test solution addition 1st | 2nd | 3rd | 4th | Amount of absorption until occurrence of leakage (g) |
| Example 1 | Production Example 1 | None | 53 | 0 | 0 | 0 | 2.0 | 318 |
| Comparative Example 1 | Production Example 2 | None | 44 | 0 | 0 | 0 | 40.0 | 280 |
| Comparative Example 2 | Production Example 3 | None | 51 | 0 | 0 | 0 | 13.8 | 306 |
| Comparative Example 3 | Production Example 4 | None | 51 | 0 | 0 | 0 | 18.0 | 302 |
| Example 3 | Production Example 1 | Liquid-acquisition diffusion sheet 20 g/m$^2$ | 43 | 0 | 0 | 0 | 3.4 | 317 |
| Example 4 | Production Example 1 | Liquid-acquisition diffusion sheet 50 g/m$^2$ | 13 | 0 | 0 | 0 | 9.8 | 310 |

TABLE 3

| | Absorbent article | | | | | | | |
|---|---|---|---|---|---|---|---|---|
| | Water-absorbent resin used | Means for improving liquid permeability | Permeation time (sec) | Leakage test Number of test solution addition 1st | 2nd | 3rd | 4th | Amount of absorption until occurrence of leakage (g) |
| Example 2 | Production Example 1 | Embossing | 46 | 0 | 0 | 0 | 1.2 | 319 |

TABLE 3-continued

| | Absorbent article | | | | | | | |
|---|---|---|---|---|---|---|---|---|
| | Water-absorbent resin used | Means for improving liquid permeability | Permeation time (sec) | Leakage test Number of test solution addition 1st | 2nd | 3rd | 4th | Amount of absorption until occurrence of leakage (g) |
| Comparative Example 4 | Production Example 2 | Embossing | 42 | 0 | 0 | 0 | 45.8 | 274 |
| Comparative Example 5 | Production Example 3 | Embossing | 49 | 0 | 0 | 0 | 8.7 | 311 |
| Comparative Example 6 | Production Example 4 | Embossing | 48 | 0 | 0 | 0 | 19.2 | 301 |

TABLE 4

| | Absorbent article | | | | | | | |
|---|---|---|---|---|---|---|---|---|
| | Water-absorbent resin used | Means for improving liquid permeability | Permeation time (sec) | Leakage test Number of test solution addition 1st | 2nd | 3rd | 4th | Amount of absorption until occurrence of leakage (g) |
| Example 5 | Production Example 1 | Slit | 20 | 0 | 0 | 0 | 28.0 | 292 |
| Comparative Example 7 | Production Example 2 | Slit | 16 | 0 | 0 | 8.5 | 55.0 | 265 |
| Comparative Example 8 | Production Example 3 | Slit | 18 | 0 | 0 | 0.4 | 42.8 | 277 |
| Comparative Example 9 | Production Example 4 | Slit | 18 | 0 | 0 | 2.2 | 38.1 | 282 |

As can be seen from the results of Tables 1 to 4, according to the present invention, it is possible to provide an absorbent article being superior in permeation rate and being inhibited from the occurrence of leakage. In the case of manufacturing an absorber and an absorbent article having the configurations of the present invention, it can be expected to provide an absorber and an absorbent article having similar performances even if the amount of the water-absorbent resin used is reduced, and there is a possibility that the manufacturing cost can be reduced.

DESCRIPTION OF REFERENCE SIGNS

1: Burette part
3: Clamp
5: Conduit pipe
10: Absorber
10*a*: Water-absorbent resin
10*b*: Hydrophilic fiber
11: Stand
13: Measuring stand
13*a*: Through-hole
15: Nylon mesh sheet
20: Core wrap
21: Burette tube
22: Cock
23: Rubber stopper
24: Cock
25: Air introducing pipe
30: Liquid-permeable sheet
31: Rear sheet
40: Support plate
41: Stand
42: Dropping funnel
43: Balance
44: Metal tray
50: Saline solution
51: Test solution
61: Burette part
61*a*: Burette
61*b*: Rubber stopper
61*c*: Cock
61*d*: Air introducing pipe
61*e*: Cock
62: Conduit pipe
63: Measuring stand
64: Measuring part
64*a*: Cylinder
64*b*: Nylon mesh
64*c*: Weight
100: Absorbent article
$S_0$: Horizontal plane
$S_1$: Inclined plane

The invention claimed is:

1. An absorbent article comprising a liquid-permeable front sheet, a liquid-impermeable rear sheet, and an absorber disposed between the front sheet and the rear sheet, wherein the absorber comprises a water-absorbent resin, and the water-absorbent resin has the following properties (A) to (C):

(A) a physiological saline retention capacity is 45 g/g or more and 70 g/g or less;

(B) a physiological saline absorption capacity under a load of 4.14 kPa is at least 13 ml/g;

(C) a value of non-pressurization DW after 5 minutes is 50 ml/g or more and 80 ml/g or less.

2. The absorbent article according to claim 1, including a means for improving liquid permeability at at least one site among the front sheet, the absorber, and a portion between the front sheet and the absorber.

3. The absorbent article according to claim 2, wherein the means for improving liquid permeability is at least one selected from the group consisting of an embossed structure, a slit structure, and an arrangement of a liquid-acquisition diffusion sheet between the front sheet and the absorber.

4. The absorbent article according to claim 2, wherein the means for improving liquid permeability is a recessed portion, a groove, or a slit structure formed by cutting out, squeezing, or penetrating the absorber in a thickness direction thereof.

5. The absorbent article according to claim 2, wherein the means for improving liquid permeability is an embossed structure provided in the absorber.

6. The absorbent article according to claim 2, wherein the means for improving liquid permeability is an arrangement of a liquid-acquisition diffusion sheet made of a hydrophilic nonwoven fabric having a basis weight of 15 $g/m^2$ or more and 75 $g/m^2$ or less between the front sheet and the absorber.

7. The absorbent article according to claim 1, wherein the absorber further comprises hydrophilic fibers.

* * * * *